United States Patent [19]

Logan

[11] Patent Number: 4,958,640

[45] Date of Patent: Sep. 25, 1990

[54] METHOD AND APPARATUS FOR CORRELATING THE DISPLAY OF INFORMATION CONTAINED IN TWO INFORMATION SIGNALS

[75] Inventor: Charles H. Logan, Woodinville, Wash.

[73] Assignee: SpaceLabs, Inc., Redmond, Wash.

[21] Appl. No.: 289,386

[22] Filed: Dec. 23, 1988

[51] Int. Cl.$^5$ ............................................... A61B 5/02
[52] U.S. Cl. ..................................... 128/671; 128/706; 128/710
[58] Field of Search ............... 128/671, 706, 708, 710; 364/413.13, 413.04, 413.05, 413.06

[56] References Cited

U.S. PATENT DOCUMENTS

| | | | |
|---|---|---|---|
| 4,519,395 | 5/1985 | Hrushesky | 128/671 |
| 4,738,264 | 4/1988 | Orlando | 128/671 |
| 4,751,931 | 6/1988 | Briller et al. | 364/413.06 |
| 4,777,960 | 10/1988 | Berger et al. | 128/706 |
| 4,803,997 | 2/1989 | Bowman | 128/671 |

Primary Examiner—Francis Jaworski
Assistant Examiner—George Manuel
Attorney, Agent, or Firm—Seed and Berry

[57] ABSTRACT

Apparatus for displaying first and second information signals includes detection circuitry for detecting the first and second signals to be displayed as well as detecting the occurrence of a predetermined phenomenon with respect to the first information signal. The first and second information signals are processed in conjunction with a timing signal to provide a display signal, wherein the display signal is adapted to be displayed using known display circuitry. Detection of the predetermined phenomenon provides an interrupt to the processing of the information signals such that the occurrence of the predetermined phenomenon can be recorded, in time correlation with the occurrence of the first and second information signals. The information signals are thereafter processed so that the ocurrence of the predetermined phenomenon can be displayed in time correlation with either the first or second information signal.

21 Claims, 5 Drawing Sheets

METHOD AND APPARATUS FOR CORRELATING THE DISPLAY OF INFORMATION CONTAINED IN TWO INFORMATION SIGNALS

DESCRIPTION

1. Technical Field

The present invention is directed toward apparatus for displaying a plurality of information signals and, more particularly, medical apparatus for displaying a heart rate and respiration rate signal and for correlating the occurrence of the QRS complex with the display of the respiration rate signal.

2. Background Art

The medical field is one of many which have benefited greatly from improvements in electrical technology. With the advent of improved data processing apparatus, improved sensing apparatus and improved methods for displaying electronic information, medical equipment, particularly medical hospital equipment, has improved in function and performance. As an example, it is now possible to provide one display medium which can readily display a plurality of information signals wherein each information signal corresponds to a sensed condition of a patient.

Along these lines, monitors used in neonatal intensive care units or operating rooms have been developed which display both the heart rate and respiration rate of the newborn patient. Further, these monitors are capable of displaying the respiration signal at a different sweep rate than that at which the heart rate signal is displayed. It is desirable to display the respiration rate at a slower sweep rate because the respiration rate is typically at least one-half the heart rate. When displayed at a slower sweep rate, the respiratory condition of the patient is readily apparent from the displayed information.

However, medical personnel and technicians have discovered that false respiration signals can result from cardiac activity (cardiovascular artifact). Because the displayed information is not a result of actual respiration, false respiration signals render meaningless any display of the respiratory condition of the patient. In an effort to identify false respiration signals which result from cardiac activity, it is desirable to provide time correlation between cardiac activity, represented by the QRS complex, and the respiration signal. Unfortunately, because the respiration rate signal is displayed at a different sweep rate than the heart rate signal, no time correlation exists between the display of the two signals. Accordingly, to provide a display of the correlation between the QRS complex and the respiration signal, additional apparatus is required.

SUMMARY OF THE INVENTION

It is a primary object of the present invention to provide a method and apparatus for displaying two signals and for monitoring the first information signal to detect a predetermined phenomenon, and indicating its occurrence in time relation with the display of the second information signal.

It is further object of the present invention to provide the above-mentioned time correlation while displaying the first and second information signals at differing sweep rates.

It is a still further object of the present invention to provide a method and apparatus for displaying a heart rate and a respiration rate signal at different sweep rates and for indicating the occurrence of the QRS complex by altering the display of the respiration rate signal.

These and other objects of the present invention are met by providing apparatus for displaying first and second information signals wherein the apparatus includes a detection circuit for detecting the occurrence of a predetermined phenomenon by monitoring the first information signal and for providing an interrupt in response to the detected phenomenon. A timing circuit is provided for providing a timing signal which creates a timing reference frame. A data display assembly responds to a display signal to provide a visual indication of a predetermined characteristic of the first and second information signals. Data processing circuitry receives the first and second information signals and the timing signals and provides therefrom the display signal. The data processing circuitry is further responsive to the interrupt signal and the timing signal to provide the display signal such that the display of the second information signal is altered thereby to indicate the occurrence of the predetermined phenomenon in real-time relationship with the predetermined characteristic of the first information signal.

In an alternative embodiment of the invention, the data processing circuitry further includes apparatus for receiving user provided input signals. The data processing circuitry is responsive to the user provided input signals for providing the display signal such that the sweep rate of the first information signal is a multiple of the sweep rate of the second information signal. The data processing circuitry is also adapted to maintain time correlation between the occurrence of the predetermined phenomenon and the display of the second information signal.

In a still further alternative embodiment of the invention, the first and second information signals represent the heart rate and respiration rate of a patient, respectively. The predetermined phenomenon represents the QRS complex and the predetermined characteristic to be displayed represents the voltage magnitude and polarity of the first and second information signals, thereby to indicate the cardiovascular and respiratory condition of the patient.

BRIEF DESCRIPTION OF THE DRAWINGS

The present invention is particularly pointed out and distinctly claimed in the numbered paragraphs appended hereto. The invention, however, both as to organization and method of practice, may best be understood by reference to the following detailed description, taken in conjunction with the drawings, in which:

DETAILED DESCRIPTION OF THE DRAWING

Figure 1:
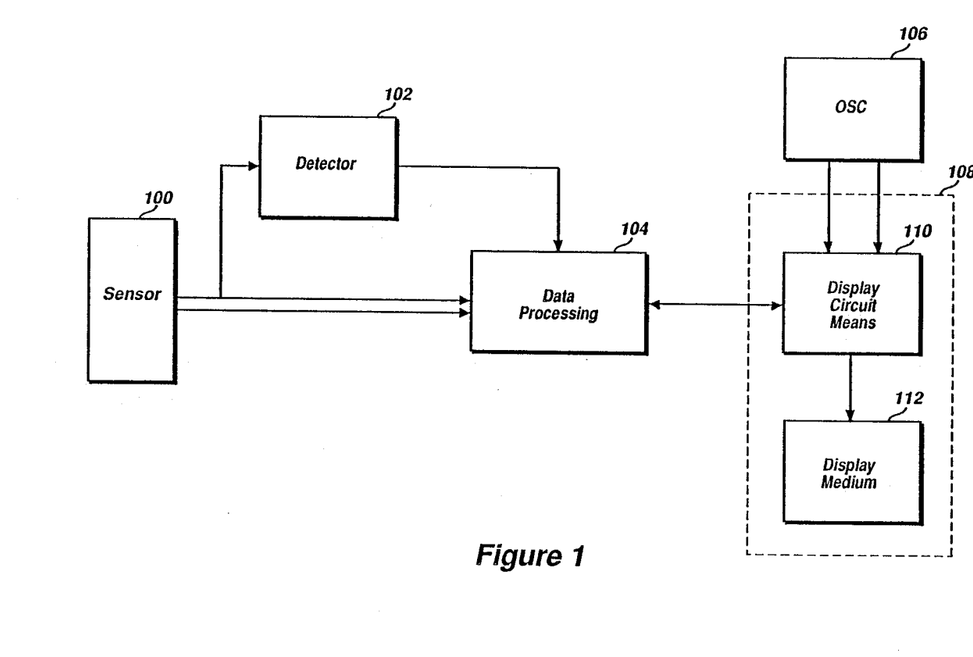
FIG. 1 is an illustrative schematic diagram of the display apparatus.

One embodiment of the apparatus which is the subject of the invention is illustrated in the block diagram of FIG. 1. The apparatus comprises a plurality of conventional sensors 100 for monitoring a patient and providing first and second signals. The first and second signals provided include information indicative of a predetermined characteristic of the patient and are therefore generally referred to herein as first and second information signals, respectively. The sensors 100 may comprise any electrical transducing device, or other electrical sensor, typically used to convert a physical characteristic, or change in physical characteristic, to an electrical signal. Although the invention is described herein by reference to a plurality of sensors 100, one sensor may be used to provide a plurality of information signals, as is known in the art.

The sensors 100 are coupled to a detector 102 and data processing circuit 104. The data processing circuit 104 is provided for storing the received first and second information signals from the sensors 100. In the presently preferred embodiment of the invention, the signal provided by the sensors 100 comprises an analog voltage signal wherein the magnitude of the voltage is indicative of the sensed condition. Accordingly, the data processing circuit 104 is constructed to digitize the analog signals and to store a plurality of digital data samples, each indicative of the voltage magnitude of the received information signal at a particular point in time. However, it will be apparent to those skilled in the art that the first and second information signals may be provided and/or stored in a plurality of formats.

The detector 102 is provided for detecting the occurrence of a predetermined phenomenon, or condition, indicated by the output from one or more of the sensors 100. The detector 102 may comprise any device, or combination of devices, constructed to detect the phenomenon of interest. As an example, the detector 102 may be comprised of devices for detecting a zero voltage level in the output signal from the sensors 100. It may further comprise devices adapted to detect a voltage level which is above a predetermined maximum. Many devices can be constructed to detect a variety of more complicated phenomenon. Further, although the detector 102 is shown and described herein as receiving a single output from the sensors 100, the detector may acutally be adapted to receive a plurality of outputs and provide an output signal in response to a combination of detected phenomenon.

The detector 102 is also coupled to the data processing circuit 104 to provide an indication that the predetermined phenomenon has been detected. In the presently preferred embodiment, the detector 102 provides an interrupt to the data processing circuit 104, as will be described more fully below.

The data processing circuit 104 is coupled to a data display assembly 108. The data display assembly 108 is provided for displaying first and second signals indicative of the voltage magnitude and polarity of the first and second information signals provided by the sensors 100. The data display 108 includes a display circuit 110 coupled to the data processing circuit 104 for receiving from the data processing circuit 104 the stored data samples described above. The display circuit 110 responds to the data samples to provide a display signal such that the first and second information signals may be displayed via a display medium 112. The display medium 112 may comprise any apparatus suitable for displaying the predetermined characteristic. In the presently preferred embodiment of the invention, the predetermined characteristic is the QRS complex as detected by the detector 102, and, accordingly, the display medium 112 is chosen to be a cathode-ray tube, or other similar device, for displaying substantially continuous, sinusoidal voltage signals.

The display circuit 110 is also adapted to receive first and second inputs from an oscillator circuit 106. The oscillator circuit 106 may comprise any timing circuit means for providing at least one timing signal, as is known in the art. As an example, the oscillator circuit 106 may comprise the combination of a crystal oscillator and know peripheral circuitry such as amplifiers, frequency dividers, buffers, phase locked loops, etc.

The timing signal is also received by the data processing circuit 104 from the display circuit 110, and is used by the data processing circuit 104 to create a timing reference frame thereby to correlate the occurrence of the predetermined phenomenon with the first and second information signals as well as to time correlate the first and second information signals with each other. In this manner, the digital data samples may be stored in a way to indicate the time correlation between the first and second information signals. The manner in which the data processing circuit 104 correlates the signals will be described in more detail below. The timing signal, received by the data processing circuit 104, may comprise a single clock signal or may comprise a plurality of clock signals.

The display circuit 110 comprises apparatus for reconstructing the analog information signals from the digital data samples provided by the data processing circuit 104. Further, the display circuit 110 may comprise apparatus for smoothing the reconstructed information signals before displaying the information signals on the display medium 112. As an example, the display circuit 110 and display medium 112 may comprise apparatus such as that shown and described in U.S. Pat. No. 4,677,431, to Michael G. Lee, entitled RASTER DISPLAY SMOOTHING TECHNIQUE, the disclosure of which is incorporated herein, in its entirety, by the foregoing reference thereto.

Figure 2:
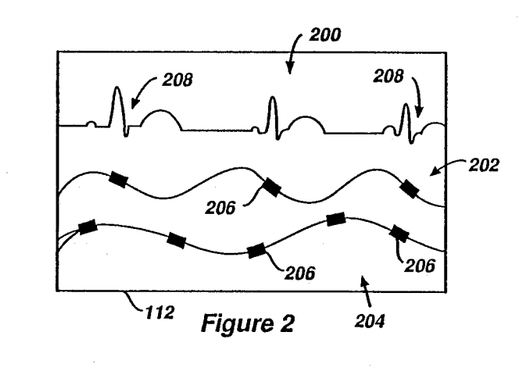
FIG. 2 is a schematic illustration of the display provided by the apparatus of FIG. 1.

In the presently preferred embodiment of the invention, the sensors 100 are constructed to sense the respiration rate and the heart rate of a patient. The detector 102 is provided for detecting the occurrence of the QRS complex, as is known in the art. An example of the display which may result from use of the subject apparatus is illustrated in FIG. 2. Therein, the waveform 200 comprises a typical waveform of the heart rate of the patient as sensed by the sensors 100 and displayed by the display medium 112. The waveform 202 represents the respiration rate of a patient. Similarly, the waveform 204 represents an alternative respiration rate of the patient and is provided only for purposes of this discussion. Typically, in operation, only one heart rate waveform and one respiration rate waveform would be provided. However, a third waveform may be provided to indicate the status of another characteristic.

Further, in the presently preferred embodiment of the invention, the predetermined phenomenon is the QRS complex. As is known in the art, the occurrence of the QRS complex may be visually observed from the display of the heart rate waveform 200. The occurrence of the QRS complex is shown generally by reference numeral 208 in FIG. 2. It is the occurrence of the QRS complex 208, as indicated by the sensed heart rate, which is to be correlated with the respiration rate waveforms 202 and 204.

As discussed above, it is typically desirable to display the heart rate waveform 200 and the respiration rate waveforms 202 and 204 at different sweep rates. Typically, the heart rate waveform 200 is displayed at a sweep rate of 25 millimeters per second and the respiration rate waveforms 202 and 204 are displayed at sweep rates of 12.5 millimeters per second. However, because of the different sweep rates, it is impossible to visually correlate the occurrence of the QRS complex by the display of the waveforms alone. Accordingly, it is desirable to intensify the respiration rate waveforms 202 and 204 at selected portions 206, each of which indicates the occurrence of the QRS complex. As will be described in more detail below, the apparatus of FIG. 1 provides a display with the desired intensification.

Since the respiration rate waveforms 202 and 204 are not displayed with the same sweep rate as the heart rate waveform 200, the intensified portions 206 of the respiration rate waveforms 202 and 204 should not coincide with the visual indication of the QRS complex 208 of the heart rate waveform 200. When the occurrences of the intensified portions 206 are simultaneous with the QRS complex portions 208 of the heart rate waveform 200, as in the respiration signal 202, the respiration signal may be a result of cardiac activity and, therefore, a false respiration signal. The graph 202 represents a false respiration signal resulting from the QRS complex. Alternatively, when the occurrences of the intensified portions 206 are not simultaneous with the QRS complex portions 208 of the heart rate waveform 200, as in the respiration rate waveform 204, then the respiration signal is not due to cardiac activity and is not a false respiration signal.

Figure 3:
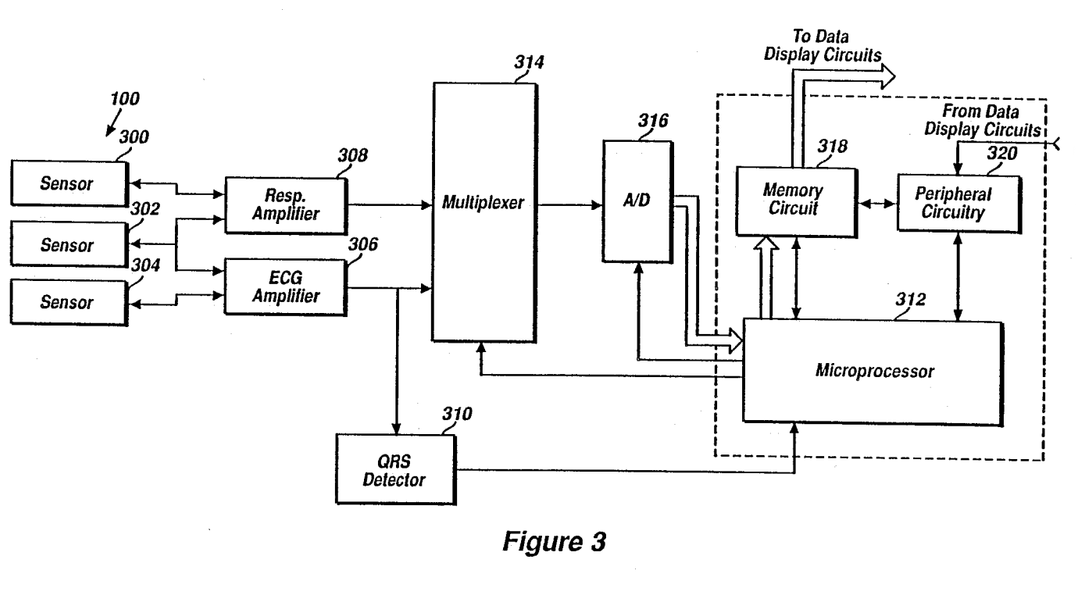
FIG. 3 is a more detailed schematic diagram of a portion of the apparatus illustrated in FIG. 1.

With reference to FIG. 3, a more detailed schematic diagram of the presently preferred embodiment of the invention is provided. Therein, the sensors 100 of FIG. 1 are shown to comprise a plurality of sensors 300-304. Each sensor 300-304 comprises an electrode adapted to be coupled to the body of a patient. A first pair of the electrode sensors 300 and 302 are positioned on the body of the patient to provide an indication of the heart rate of the patient. Similarly, a second pair of the electrode sensors 302 and 304 are positioned on the body of the patient to provide an indication of the respiration rate of the patient.

As is known in the art, the respiration rate is sensed by the electrode sensors 300-304 by monitoring the frequency at which the resistivity of the patient's thorax changes. That is, the time period between increases and decreases in resistivity indicates the time period between breaths. The respiration rate is indicated by the frequency of change in resistivity intermediate the electrode sensors 300-302 and the electrode sensors 302-304, respectively.

Output from the electrode sensors 300 and 302 are provided to an ECG amplifier 306 so that the heart rate signal provided from the sensors may be amplified. In a similar manner, the signals from the sensors 302 and 304 are provided to a respiratory amplifier 308 so that the signals may be amplified. The amplifiers 306 and 308 comprise voltage amplifiers which detect and amplify changes in resistivity between the respective pairs of sensors 300-304 thereby to detect the heart rate and respiration rate of the patient. Accordingly, the output from the ECG amplifier 306 and the output from the respiration amplifier 308 each comprise continuous voltage signals wherein the frequency of the voltage signal indicates the heart rate and respiration rate of the patient, respectively. Both the ECG amplifier 306 and the respiration amplifier 308 may comprise conventional devices readily available to those skilled in the art.

The ECG amplifier 306 is coupled to a conventional QRS detector 310. The QRS detector 306 is provided for detecting the QRS complex as is known in the art. Typically, the QRS detector may comprise apparatus for continually monitoring the slope, amplitude and duration of the ECG amplifier output and for comparing these monitored values to predetermined quantities. As such, the QRS detector may comprise differentiators, comparators, filters, timers, amplifiers and other conventional circuitry. It will be apparent to those skilled in the art that an acceptable QRS detector may be readily provided from known slope, amplitude and duration characteristics of the heart rate signal. Further, as discussed above, many other detectors may be provided for detecting other phenomenon.

The output from the QRS detector is provided to a microprocessor 312. The microprocessor 312 receives the output from the QRS detector 310 at an interrupt input as will be described more fully below.

The output from the ECG amplifier 306 and the respiration amplifier 308 is coupled to a multiplexer 314. The multiplexer 314 receives a control signal from the microprocessor 312 which control signal selects either the ECG amplifier 306 output or the respiration amplifier 308 output to be provided as the output of the multiplexer 314. The multiplexer 314 provides its output to an analog-to-digital (A/D) converter 316. The analog-to-digital converter 316 is provided for converting the output from the multiplexer 314 to a multiple bit digital data sample wherein the binary value of the digital data is indicative of the magnitude of voltage at the multiplexer output at the time of conversion, as is known in the art. The analog-to-digital converter 316 also receives a control signal from the microprocessor 312, which control signal instructs the analog-to-digital converter 316 when the output from the multiplexer 314 is to be converted to the multiple bit data sample.

The multiplexer 314, the A/D converter 316 and the microprocessor 312 cooperate to digitize the information signals provided by the amplifiers 306 and 308 to provide a plurality of data samples. Both the multiplexer 314 and the A/D converter 316 may comprise conventional devices readily available to those skilled in the art. Alternatively, other devices, or device combinations, could be constructed for digitizing the signals provided by the amplifiers 306 and 308. Additionally, if an alternative method of storing the signals is selected, as discussed above, then alternative signal processing may be required before storage.

The output from the analog-to-digital converter 316 is provided to a memory circuit 318, via the microprocessor 312, for storage therein. The memory circuit 318 is also coupled to the microprocessor 312 for receiving control signals therefrom and for providing data thereto. The microprocessor 312 controls the analog-to-digital converter 316 and the memory circuit 318 to store the digitized heart rate and respiration rate signals provided by the ECG amplifier 306 and the respiration amplifier 308. Accordingly, the memory circuit 318 may comprise random access memory (RAM) for storing the respiration data samples and the heart rate data samples. Further, the memory circuit 318 may comprise read only memory for storing program information for use by the microprocessor 312.

Additionally, the memory circuit 318 may comprise any peripheral circuitry, such as memory controllers, timers, buffers, latches, etc., needed for performing the operations described herein.

The microprocessor 312 is coupled to peripheral circuitry 320 which may comprise any circuitry for interfacing the microprocessor 312 with the memory circuit 318 and for interfacing the microprocessor 312 with other devices. Particularly, the microprocessor 312 receives the timing signal from the data display assembly 108 via the peripheral circuitry 320, as will be described more fully below. The peripheral circuitry 320 may comprise conventional input/output devices, coupling means, latches, buffers, timing circuits, counters and other circuitry readily available to those skilled in the art.

Figure 5:
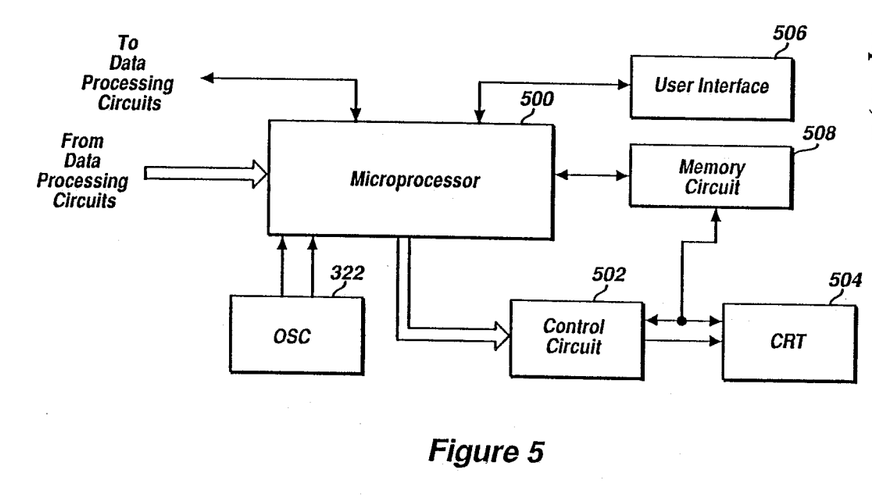
FIG. 5 is a more detailed schematic diagram of portions of the apparatus illustrated in FIG. 1.

The microprocessor 312 and the memory circuit 318 of FIG. 3 are each electrically coupled to a microprocessor 500, illustrated in FIG. 5. The microprocessor 500 is coupled to a control circuit 502 and a cathode-ray tube 504 for displaying respiration and heart rate signals of the patient. The control circuit 502 and the cathode-ray tube 504 may each comprise portions of the display circuit 110 and the display medium 112, respectively, described hereinabove. The microprocessor 500 is responsive to the heart rate and respiration rate data samples stored in the memory circuit 318 to provide a display signal to the control circuit 502, as will be described below.

Also, the microprocessor 500 is coupled to receive first and second clock signals from an oscillator circuit 322. The oscillator circuit 322 operates and performs in all manners similar to the oscillator 106 illustrated and described by reference to FIG. 1. More particularly, the oscillator circuit 322 is constructed to provide first and second periodic clock signals each having separate predetermined periods. In the presently preferred embodiment of the invention, the period of the first clock signal is an integral multiple (eight herein) of the period of the second clock signal. The oscillator circuit 322 provides the first clock signal at a frequency of approximately 56 cycles per second and provides the second clock signal at a frequecy of approximately 448 cycles per second. However, the period of the first clock signal may be a non-integral multiple of the period of the second clock signal without departing from the scope and spirit of the invention.

The first and second clock signals are provided to the microprocessor 312 from the microprocessor 500 via the peripheral circuit 320 and comprise the timing signal mentioned above. The microprocessor 312 is adapted to control the multiplexer 314 and the analog-to-digital converter 316 to digitize a heart rate data sample upon each occurrence of the second clock signal. The microprocessor 312 is also adapted to control the multiplexer 314 and the analog-to-digital converter 316 to digitize one respiration rate data sample during each occurrence of the first clock signal.

Figure 4:
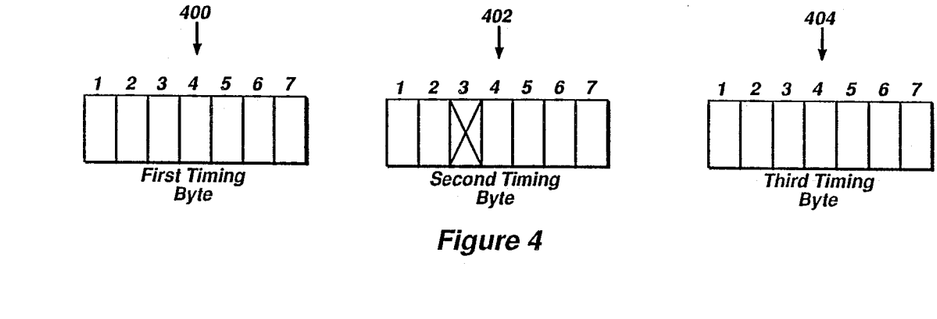
FIG. 4 is a plurality of timing bytes generated by the apparatus of FIG. 3.

A particularly novel feature of the invention is the manner in which the microprocessor 312 correlates the occurrence of the QRS complex with the heart rate and respiration rate samples to be stored in the memory circuit 318. The microprocessor 312 responds to the first and second clock signals to provide a plurality of timing bytes, three timing bytes being diagramatically illustrated in FIG. 4. A timing byte begins upon the occurrence of each first clock signal and has therein eight periods, each corresponding to one occurrence of the second clock signal. The timing byte indicates whether a QRS interrupt, from the QRS detector 310, has been received by the microporcessor 312 during a specified occurrence of the first clock period. Further, the timing byte may be used to indicate the exact interval during the first clock period when the QRS interrupt was received. With reference to FIG. 4: the timing byte 400 indicates that a QRS interrupt was not detected; the timing byte 402 indicates that a QRS interrupt was detected during the third period of the timing byte; and the timing byte 404 indicates that no QRS interrupt was detected.

In the presently preferred embodiment of the invention, the timing byte need only indicate whether a QRS interrupt was detected any time intermediate any particular occurrences of the first clock signal, i.e., the exact interval of the timing byte when the interrupt occurs is not required for operation of the subject embodiment. This is because the respiration rate data samples are only taken upon each occurrence of the first clock signal. The timing bytes therefore indicate when, in time correlation to the respiration rate data sample, the QRS interrupt occurred thereby indicating when the QRS complex occurred. As mentioned above, the timing bytes are stored in the memory circuit 318 in a manner to indicate the time correlation between the timing bytes and the data samples. This may be done, for example, by using a dual addressing scheme wherein one address is indicative of the relative time period in which a sample was taken as is known in the art.

Generally, the cathode-ray tube 504 comprises a plurality of pixels with vertical raster lines as is known in the art. In the presently preferred embodiment of the invention, 720 pixels, or raster lines, are provided horizontally across the cathode-ray tube 504, of which 512 are used to display information signals. As is known in the art, the plurality of pixels cooperate to display an image, here the heart rate and respiration rate waveforms 200, 202 and 204 of FIG. 2. The control circuit 502 combines a plurality of vertical pixels to provide a raster line. Each raster line contains information relative to the positioning of the heart rate and respiration rate signal, i.e., whether a pixel is energized or not, during a specified point in time. The combination of raster lines cooperate to display the heart rate and respiration rate signals.

As mentioned above, it is desirable to display the heart rate signal at a sweep rate of approximately 25 millimeters per second while the respiration rate signal is generally displayed at a sweep rate of approximately about 12.5 millimeters per second. However, in the preferred embodiment of the invention, a user may provide various sweep rates via a user interface 506. The user interface 506 is provided for interfacing a user with the microprocessor 500 and the control circuit 502, as is known in the art. The user interface 506 may comprise a keyboard, or other means, for translating user input to data signals usable by the microprocessor 500.

The sweep rates provided by the user interface 506, as well as data provided by the microprocessor 500, may be stored in a memory circuit 508. Like the memory circuit 318, the memory circuit 508 may comprise randomaccess memory, read-only memory and necessary peripheral circuitry.

The microprocessor 500 responds to the desired sweep rate to average a plurality of respiration rate data samples before building the raster lines. In this manner, the respiration rate signal is displayed at a sweep rate which varies from that of the heart rate signal. As the data samples are averaged, the timing bytes are monitored to indicate the occurrence of the QRS complex. If the QRS complex occurs during any one of the plurality of timing bytes corresponding to the plurality of respiration data samples which may be averaged, then the averaged sample is considered the sample which corresponds in time to the time that the QRS complex occurred. The microprocessor 500 therefore alters the display signal provided to the control circuit 502 such that the display of the subject sample indicates the occurrence of the QRS complex.

Figure 6:
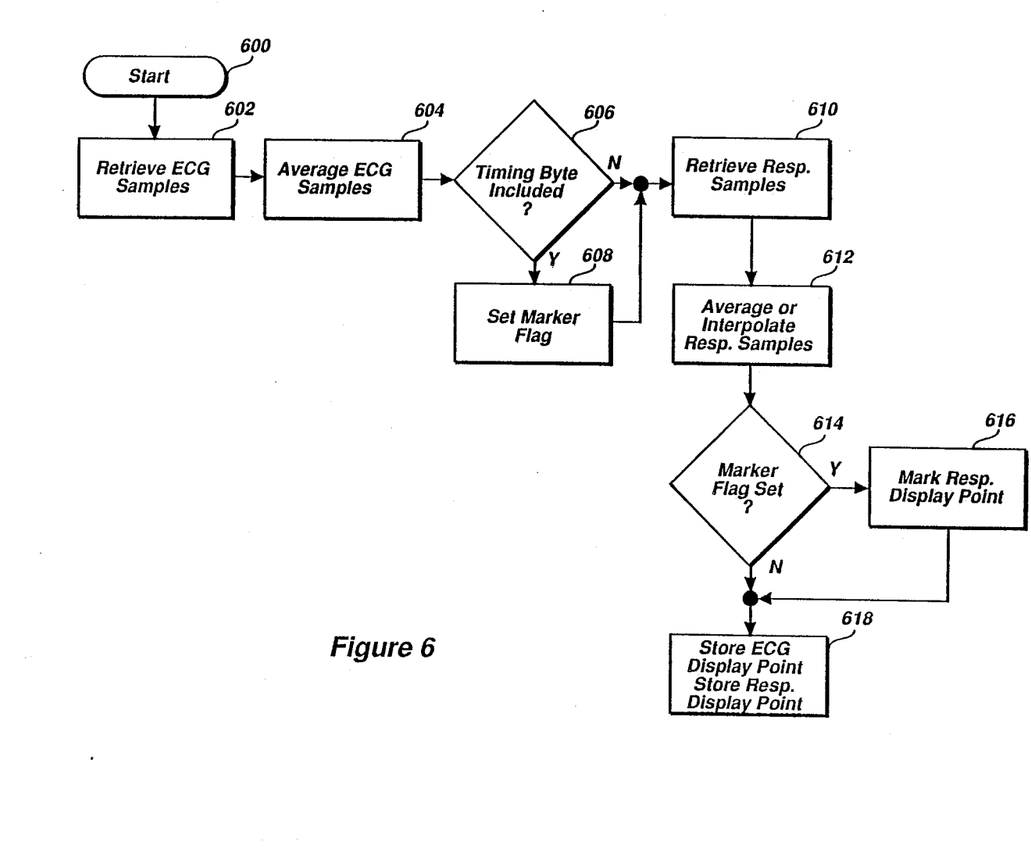
FIG. 6 is a decision flow diagram illustrating the method implemented by the apparatus of FIG. 1.

The particular method implemented by the microprocessor 500 is illustrated with respect to FIG. 6. Therein, the microprocessor 500 begins analysis of the data samples at step 600. The microprocessor is initialized using procedures which are standard in the microprocessor art. The microprocessor 500 then retrieves a plurality of ECG data samples from the memory circuit 318 along with the ECG sweep speed from the memory circuit 508 (step 602). The plurality of ECG data samples are averaged (step 604) in accordance with the desired ECG sweep speed, as described in the afore-referenced U.S. Pat. No. 4,677,431. The averaged samples may be restored in the memory circuit 508. The microprocessor 500 thereafter determines whether any timing byte corresponding to the plurality of averaged data samples indicates the occurrence of the QRS complex (step 606) and, if so, sets a marker flag (step 608). As is known in the art, the marker flag is used to indicate the occurrence of an event, herein the occurrence of the QRS complex.

After averaging the ECG samples, as described above, the microprocessor 500 retrieves a plurality of respiration samples from the memory circuit 318 along with the desired respiration sweep speed from the user interface 506 (step 610). The plurality of respiration data samples retrieved are time correlated to the averaged heart rate samples as described above. The respiration data samples are averaged, or interpolated, as required by the respiration sweep speed (step 612).

The microprocessor 500 then checks the marker flag (step 614), and if the marker flag is set, the microprocessor 500 marks the respiration display point (step 616) such that this display point can be highlighted to indicate the occurrence of the QRS complex. By so marking the display point, the time correlation between the occurrence of the QRS complex and the respiration rate signal is maintained. The microprocessor 500 returns to step 602 to continue the method of FIG. 6 until operation is terminated by the user.

In the presently preferred embodiment of the invention, the respiration signal is highlighted by increasing the intensity thereof. However, other methods can be used for highlighting the respiration signal to indicate the occurrence of the QRS complex. As an example, the intensity of the respiration signal may be decreased, the display surface of the respiration signal may be increased to display a bubble or other structure thereby indicating the QRS complex, etc.

While only several presently preferred embodiments of my novel method and apparatus for correlating the display of information contained in two information signals have been described in detail herein, many modifications and variations thereof will readily become apparent to those skilled in the art. It is my intention, therefore, by the claims appended hereto, to embody all such modifications and variations as fall within the true scope and spirit of my invention.

I claim:

1. An apparatus for displaying first and second information signals, each with reference to the occurrence of a predetermined phenomenon, comprising:
   detection means for monitoring the first information signal to detect the predetermined phenomenon and for providing an interrupt signal in response thereto;
   timing circuit means for providing at least one timing signal to create a timing reference frame;
   data display means, responsive to a display signal, for providing a visual indication of a predetermined characteristic of the first and second information signals; and
   data processing means for receiving the first and second information signals and the at least one timing signal to provide the display signal, said data processing means being responsive to the interrupt signal and the at least one timing signal to alter the display signal such that the display of the second information signal is also altered thereby to indicate the occurrence of the predetermined phenomenon in real-time relationship with the display of the predetermined characteristic of the second information signal.

2. The apparatus of claim 1 wherein said data processing means comprises input means for receiving user provided input signals, said data processing means being responsive to the user provided input signals for providing the first information signal at a first sweep rate and for providing the second information signal at a second sweep rate such that the first sweep rate is a multiple of the second sweep rate, said data processing means being also adapted to maintain a time correlation between the occurrence of the predetermined phenomenon and the second information signal.

3. The apparatus as recited in claim 2 wherein the first and second information signals have voltage magnitudes and wherein the predetermined characteristic is the magnitude of voltage of the first and second information signals, said data processing means including means for providing the display signal such that the first and second information signals are displayed as graphs of continuous signals.

4. The apparatus as recited in claim 3 wherein said data display means includes means for providing a variable intensity display in response to the display signal and wherein selected portions of the variable intensity display of the second information signal are intensified in response to the display signal to indicate the occurrence of the predetermined phenomenon.

5. The apparatus as recited in claim 4 wherein the first and second information signals comprise heart rate and respiration rate signals of a patient, respectively, said apparatus further comprising sensor means for providing a heart rate output signal indicative of the heart rate of the patient, said sensor means being further adapted to provide a respiration rate output signal indicative of the respiration rate of the patient.

6. The apparatus as recited in claim 5 wherein the heart rate signal is indicative of a QRS complex and wherein the predetermined phenomenon is the occurrence of the QRS complex indicated by the heart rate signal, said detection means further comprising means for detecting the QRS complex.

7. An apparatus for monitoring and displaying the respiration and heart rate of a patient, comprising:
   sensor means for providing a heart rate output signal indicative of the heart rate of the patient, said sensor means being also for providing a respiration rate output signal indicative of the respiration rate of the patient, wherein both the heart rate and respiration rate output signals comprise alternating current voltage signals having a varying voltage magnitude;
   QRS signal detector means responsive to said sensor means for detecting the occurrence of a QRS complex and for providing in response thereto a QRS interrupt signal;
   timing signal generator means for providing a timing signal, said timing signal comprising a periodic signal having a predetermined period;
   data processing means for storing the output from said sensor means, said data processing means being responsive to the timing signal to obtaining store a plurality of respiration rate data samples and a plurality of heart rate data samples, wherein each said respiration rate data sample is indicative of the value of the voltage of the respiration rate output signal at the time the respiration rate data sample is obtained and wherein each heart rate data sample is indicative of the value of the voltage of the heart rate output signal at the time the heart rate data sample is obtained, said data processing means being further responsive to the QRS interrupt signal for providing a timing byte signal wherein the timing byte signal indicates the timing of the occurrence of the QRS complex relative to the timing signal; and
   data display means for providing a visual indication of the respiration and heart rate of the patient, said data display means including a display medium for providing a variable intensity display and being responsive to the timing signal and the plurality of heart rate and respiration rate data samples for displaying a heart rate and respiration rate signal on said display medium such that the positioning of the signals is indicative of the sensed heart rate and respiration rate, said data display means being further responsive to the timing byte signal to alter the intensity of a portion of the respiration signal to thereby indicate the times of the occurrences of the QRS complex.

8. The apparatus as recited in claim 7 wherein said data display means comprises input means for receiving user provided input signals, said data display means being responsive to the user provided input signals for displaying the heart rate and respiration rate signals at different sweep speeds, said data display means being further adapted to maintain correlation between the timing byte and the respiration signal to thereby maintain correlation between the occurrence of the QRS complex and the respiration signal.

9. The apparatus as recited in claim 8 wherein said data processing means comprises:
   a multiplexer coupled to said sensor means and adapted to selectively provide either the heart rate output signal or the respiration rate output signal as said multiplexer output signal;
   an analog-to-digital converter coupled to receive the output from said multiplexer and to provide in response thereto the heart rate and respiration rate data samples; and
   first microprocessor circuit means for controlling said multiplexer and said analog-to-digital converter, said first microprocessor circuit means being also adapted to receive and store the heart rate and respiration rate data samples, said first microprocessor circuit means being responsive to the QRS interrupt signal for providing the timing byte signal.

10. The apparatus as recited in claim 8 wherein said timing signal generator means comprises first and second timing circuits, said first timing circuit being adapted to provide a first clock signal at a rate of 56 cycles per second and said second timing circuit being adapted to provide a second clock signal at a rate of 448 cycles per second, the first and second clock signals comprising the timing signal, the first clock signal being used to indicate the beginning of a timing byte and the second clock signal being used to indicate a period during the timing byte wherein the QRS interrupt signal is provided.

11. The apparatus as recited in claim 8 wherein said data display means further comprises means for providing the display signal such that the displayed heart and respiration rate signals do not appear jagged.

12. An apparatus for monitoring and displaying the respiration and heart rate of a patient, comprising:
   first, second and third sensors each adapted to be coupled to the patient;
   an electrocardiograph amplifier coupled to said first and second sensors for generating a heart rate signal indicative of the heart rate of the patient and amplifying the heart rate signal to provide an amplified heart rate signal as its output wherein the time rate of change of the voltage magnitude of the amplified heart rate signal is indicative of the heart rate of the patient;
   a respiration amplifier coupled to said first and third sensors for generating a respiration rate signal indicative of the respiration rate of the patient and for amplifying the respiration rate signal to provide an amplified respiration signal as its output, wherein the time rate of change of the amplified respiration rate signal is indicative of the patient's respiration rate;
   a QRS signal detector coupled to receive the amplified heart rate signal and adapted to provide in response thereto a QRS interrupt indicating the occurrence of the QRS complex;
   a multiplexer coupled to receive the amplified heart rate signal and the amplified respiration signal and responsive to a multiplexer control signal to provide a single multiplexer output corresponding to either the amplified heart rate signal or the amplified respiration signal;
   an analog-to-digital converter responsive to an A/D control signal for receiving the multiplexer output from said multiplexer and providing a multiple bit digital output indicative of the voltage magnitude of the multiplexer output, wherein each said multiple bit digital output provided comprises a data sample being a heart rate sample if the multiplexer output is the amplified heart rate signal and the data sample being a respiration rate sample if the multiplexer output is the amplified respiration signal;
   a timing generator for providing first and second clock signal outputs, said first and second clock signals each comprising periodic signals having first and second predetermined periods, respectively, wherein said first period is an integral multiple of said second period;

first microprocessor circuit means for receiving and storing the heart rate samples and the respiration rate samples, said first microprocessor circuit means being adapted to receive the first and second clock signals and being responsive to the first and second clock signals to provide the multiplexer control signal and the A/D control signal such that a heart rate sample is provided from said analog-to-digital converter with each occurrence of the second clock signal and a respiration rate sample is provided from said analog-to-digital converter with each occurrence of the first clock signal, said first microprocessor circuit means including random access memory and being further adapted to store the heart and respiration rate samples provided from said analog-to-digital converter in said memory, said first microprocessor circuit means being responsive to the QRS interrupt for providing a timing byte wherein the timing byte indicates the occurrence of the QRS complex relative to the first and second clock signals;

display means responsive to a display signal for providing a visual indication of the respiration and heart rate of the patient; and second microprocessor circuit means for providing the display signal in response to the heart and respiration rate samples, the first and second clock signals and the timing byte, said second microprocessor circuit means being adapted to retrieve a plurality of heart rate and respiration rate samples and a plurality of timing bytes from said memory, said second microprocessor circuit means being responsive to the plurality of heart rate and respiration rate data samples for creating the display signal wherein the display signal contains information for reconstructing heart and respiration signals and for positioning the reconstructed heart signal and the reconstructed respiration signal on said display means such that the positioning of the signals indicates their voltage magnitude, said second microprocessor circuit means being further responsive to the timing byte to alter the display signal such that the respiration signal is intensified upon each occurrence of the QRS complex.

13. The apparatus as recited in claim 12 wherein said second microprocessor circuit means comprises input means for receiving user provided input signals, said second microprocessor circuit means being responsive to the user provided input signals for averaging a plurality of the respiration rate samples to provide a plurality of averaged respiration rate samples and for providing the display signal such that the sweep rate at which the heart rate signal is displayed is a multiple of the sweep rate at which the respiration rate signal is displayed, said second microprocessor circuit means being further adapted to maintain a time correlation between the averaged respiration rate samples and the occurrences of the timing bytes so that the occurrence of the QRS complex is also maintained in time correlation with the averaged respiration rate samples.

14. An apparatus as recited in claim 13 wherein said timing generator includes first and second timing circuits, said first timing circuit being adapted to provide the first clock signal at a rate of 56 cycles per second and said second timing circuit being adapted to provide the second clock signal at a rate of 448 cycles per second.

15. An apparatus as recited in claim 14 wherein said second microprocessor circuit means further comprises means for providing the display signal such that the displayed heart and respiration rate signals do not appear jagged.

16. A method for displaying first and second information signals, comprising the steps of:

providing at least one timing signal to create a timing reference frame;

detecting a predetermined phenomenon indicated by a first predetermined characteristic of the first information signal and providing an interrupt signal in response to the detection of the first predetermined phenomenon;

providing a timing byte to indicate a real-time correlation between the occurrence of the predetermined phenomenon and the status of a second predetermined characteristic of the second information signal;

responding to a display signal to provide a visual indication of a third predetermined characteristic of the first information signal and to provide a visual indication of the second predetermined characteristic of the second information signal, wherein the visual indication is provided on a display medium;

providing the display signal in response to the first and second information signals and the timing signal wherein the display signal includes information for building raster lines on the display medium and wherein each raster line contains information relative to the positioning of the first and second information signals on the display medium and the combination of raster lines cooperate to provide the visual indication of the first, second and third predetermined characteristics; and responding to the timing byte and the timing signal to alter the display signal such that the display of the second information signal is altered thereby to indicate the occurrence of the predetermined phenomenon in real-time relationship with the second predetermined characteristic of the second information signal.

17. The method as recited in claim 16, further comprising the steps of:

receiving user provided input signals and responding to the user provided input signals for providing the display signal such that the sweep rate at which the first information signal is displayed is a multiple of the sweep rate at which the second information signal is displayed; and maintaining correlation between a multiple of timing bytes and the respiration signal to maintain real-time correlation between occurrence of the predetermined phenomenon and the respiration signal.

18. The method as recited in claim 17 wherein the third and second predetermined characteristics are the voltage magnitude of the first and second information signals, respectively.

19. The method as recited in claim 18 wherein the step of providing the display signal comprises the substep of altering the display signal such that the second information signal is intensified to indicate the occurrence of the predetermined phenomenon.

20. The method as recited in claim 19 wherein the first and second signals comprise heart rate and respiration rate signals of a patient, respectively, said method further comprising the step of sensing the heart rate and respiration rate and providing the first and second information signals indicative of the heart rate and the respiration rate of the patient, 21. The method as recited in claim 20 wherein the predetermined phenomenon is a QRS complex in the heart rate signal and wherein the step of detecting the predetermined phenomenon comprises the substep of detecting the QRS complex.

* * * * *